United States Patent [19]

Proctor et al.

[11] 4,106,493

[45] Aug. 15, 1978

[54] BIPHASIC OTOSCOPIC AIR STIMULATOR FOR PERFORMING CLINICAL CALORIC TESTS

[75] Inventors: Leonard R. Proctor, Chicago; Raymond G. Byrnes, Oak Lawn, both of Ill.

[73] Assignee: The United States of America as represented by the Department of Health, Education and Welfare, Washington, D.C.

[21] Appl. No.: 759,172

[22] Filed: Jan. 13, 1977

[51] Int. Cl.² .............................................. A61B 19/00
[52] U.S. Cl. .................................. 128/2 R; 128/2 N; 128/2.1 M; 128/9; 128/401
[58] Field of Search .......... 128/2 R, 2 N, 2 Z, 2.1 M, 128/9, 212, 254–257, 399–402

[56] References Cited

U.S. PATENT DOCUMENTS

| | | | |
|---|---|---|---|
| 1,693,021 | 11/1928 | Cameron | 128/9 |
| 3,384,076 | 5/1968 | Speelman | 128/9 |
| 3,698,387 | 10/1972 | Moore et al. | 128/9 |
| 3,934,578 | 1/1976 | Heine | 128/9 |
| 3,942,515 | 3/1976 | Servos et al. | 128/2 R |
| 3,995,620 | 12/1976 | Epley | 128/2 R |

FOREIGN PATENT DOCUMENTS 182,457  6/1922  United Kingdom ..................... 128/256

OTHER PUBLICATIONS

Aantaa, "Caloric Test with Air", Acta Otol., Supp 224, vol. 24, 1967, pp. 82–85.
Gates et al., "The Thermoelectric Air Stimulator" Arch. Otol., vol. 92, Jul. 1970, pp. 80–84.
Proctor et al., "Construction . . . Air Stimulator for Caloric Vest. Testing", Laryngoscope, vol. 86, No. 1, pp. 126–131, Jan. 1976.
Proctor et al., "A Method for Adjusting . . . Air Coloric Test", Trans. Am. Accd. of Opht. & Otol., Mar.–Apr. 1976, pp. 210–222.
Proctor et al., "Irrigation Handle With Temp. Sensor . . . ", Laryngoscope, vol. 83, 1973, pp. 1717–1721.
Albemaz et al., "The Use of Air . . . Stimulation", Laryngoscope, vol. 82, 1972, pp. 2198–2203.

*Primary Examiner*—Lee S. Cohen
*Attorney, Agent, or Firm*—Browdy and Neimark

[57] ABSTRACT

A caloric testing apparatus for introducing heated or cooled air, under direct visual control, into the outer ear canal of a human subject for purposes of testing inner ear balance mechanisms. The device includes a speculum for observing the ear canal during the flow of air, thereby assuring proper direction of the impinging air jet. The apparatus includes temperature-controlled liquid baths for providing hot or cold air, and has arrangements for providing suitably timed irrigation periods, adjustable so as to control the magnitudes of the caloric stimulations. Measurements can be made by the electrical recording of eye movements for accurate measurement of nystagmic response intensity.

10 Claims, 2 Drawing Figures

BIPHASIC OTOSCOPIC AIR STIMULATOR FOR PERFORMING CLINICAL CALORIC TESTS

FIELD OF THE INVENTION

This invention relates to clinical caloric air testing apparatus, and more particularly to an apparatus for observing the ear canal of a patient while the canal is being irrigated with heated or cooled air or other gas during testing for disordered vestibular function.

BACKGROUND OF THE INVENTION

It has been demonstrated that air can be used, instead of water, to irrigate the aural canal during routine performance of the clinical caloric tests. Advantages obtained by the use of air are: convenience to the operator, better patient acceptance, and applicability in situations where water is contra-indicated, such as following otological surgery or in cases of tympanic membrane perforation or external otitis. However, some clinicians feel that air irrigations may sometimes fail to produce a sufficiently intense stimulation of the labyrinth, and those interested in quantitative assessment of vestibular function may question how accurately and uniformly the labyrinthine stimulus can be reproduced when using air as the irrigation fluid.

When substituting air for water as the irrigation fluid, it should be expected that certain adjustments in the technique would be required because of the marked differences in their thermal properties. For example, unless the difference between irrigation temperature and body temperature is increased, responses to air irrigations are considerably weaker than responses to water. It has been found that irrigations with air for 60 seconds at a flow rate of 8 liters per minute and temperatures of 50° C and 24° C were required to produce nystagmic responses equal in intensity to those obtained in the same subjects by water irrigations at 44° C and 30° C for 30 seconds. Furthermore, in order to ensure adequate control of air irrigation temperature it is necessary to take certain precautions in the design and operation of the irrigation equipment. Thin-walled irrigation nozzles or low flow rates may allow significant instability in the control of the temperature of the air delivered into the aural canal.

Another consideration worth noting is the change in the heat flow at the aural canal surface caused by moisture. When a wet canal is irrigated with dry air, heat is taken up by the evaporation of surface moisture. As a result, the effect of a cold air irrigation is exaggerated, and the effect of a hot air irrigation is diminished. However, repetition of the hot air irrigations will dry the canal, and thereafter the irrigations are adequate to elicit the expected response.

The necessity of irrigating a moist ear canal may arise following removal of cerumen by douching or in the presence of external otitis. Under thes circumstances, the initial irrigations with hot air may serve only to dry the canal; a second hot irrigation would then be required to produce the desired stimulation. A tympanic perforation may also interfere with the air caloric test, especially if the perforation is large. In such cases, it is important to avoid directing the air jet through the perforation because this will reduce chances of producing a proper stimulation and usually will be painful to the patient.

Finally, certain precautions seem to be indicated in view of special heat transfer properties related to "jet effects" of air. When Fitzgerald and Hallpike* introduced their method of water irrigations, they emphasized the importance of a "mass" irrigation which bathed the entire aural canal surface with water of uniform temperature, so that a controlled and repeatable heat transfer effect would be achieved. Under such conditions heat would be expected to flow uniformly in all directions away from the aural canal surface. The temperature difference developing across the lateral semicircular canal is attended with endolymph density differences which act to displace the endolymph-cupula system, thereby stimulating the receptor organ. However, when small volumes of water are used ("minimal" caloric test), care must be taken to direct the flow against the posterior-superior part of the aural canal, adjacent to the eardrum, because of the more localized conduction of heat. Otherwise, as pointed out by Dohlman*, temperature changes in the lateral semicircular canal area might be inadequate to induce nystagmus despite the presence of a healthy lateral semicircular canal organ. The result would be a "false negative" caloric reaction and the test might be misinterpreted to indicate vestibular paralysis in the ear stimulated.

* Fitzgerald et al, "Studies in Human Vestibular Function. I. Observations on the Directional Preponderance ("Nystagmusbereitschaft") of Caloric Nystagmus Resulting from Cerebral Lesions", Brain, 65:115–137, 1942.
* G. Dohlman, "Physikalische und Physiologische Studien zur Theorie des Kalorischen Nystagmus." Acta Otolaryngol., Suppl. 5,pp.1–196, 1925.

During air caloric testing the concentration of heat flow upon a small area of the aural canal could occur, in the area of jet impingement. For this reason, the operator should guard against a "false negative" test by carefully directing the jet of air against the postero-superior aural canal, preferably by visual guidance.

In order to explore the practical importance of this question, nystagmus responses to properly directed air irrigations were compared with responses to deliberately misdirected irrigations in the same ears of several normal subjects. Variations in response intensity were clearly demonstrated, though such variations were not always consistent and were not usually profound. Nevertheless, in the interest of providing uniform and repeatable caloric stimulations, care should be taken to aim the air jet at the posterosuperior aural canal surface throughout the irrigation period.

A preliminary search of the known prior art reveals the following U.S. patents as representing the best prior art found relating to the subject matter of the present invention:

Zeng, No. 1,062,698
Carroll, No. 1,106,699
Harris, No. 1,346,200
De Zeng, No. 1,588,791 McGerry No. 2,039,546

The following publications also appear to be significant in showing the known state of the art:

Albernas et al, "The Use of Air in Vestibular Caloric Stimulation", Laryngoscope, 82:2198–2203, 1972.

Capps et al, "Evaluation of the Air Caloric Test as a Routine Examination Procedure", Laryngoscope, 83:1013–1021, 1973.

Meurman et al, "The Caloric and Turning Tests After the Fenestration Operation", Acta Otolaryngol., Supp. 100, pp. 144–153,1952.

Aanta, "Caloric Test with Air", Acta Otolaryngol., Supp. 224, pp. 82–85, 1967.

Aschen, "The Caloric Test, a Nystagmographic Study", Acta Soc. Med. Upsal., 60:99–112, 1955.

Fitzgerald et al, "Studies in Human Vestibular Function. I. Observations on the Directional Preponderance ("Nystagmusbereitschaft") of Caloric Nystagmus Resulting from Cerebral Lesions, Brain, 65:115–137, 1942.

Dohlman, "Physikalische und Physiologische Studien zur Theorie des Kalorischen Nystagmus", Acta Otolaryngol., Supp. 5, pp. 1–196, 1925.

SUMMARY OF THE INVENTION

Accordingly, objects of the present invention are to overcome deficiencies in the prior art such as indicated above and to provide a means for introducing air or other gases, under direct visual control, into the outer ear canal of human subjects for purposes of testing inner ear balance mechanisms.

Another object of the invention is to provide an improved caloric ear irrigation apparatus having means for observing the ear canal during flow of air, thereby assuring proper direction of the air jet and avoidance of erroneous effects or variations in heat flow resulting from misdirection of the jet, as mentioned above, the apparatus including provision for switching the temperature of the irrigation air stream in a reliable and precise manner between pre-selected temperatures at specified times, whereby to enable the operator to control and adjust the stimulus intensity of the caloric test in a reliable and convenient manner, and wherein a key feature of the apparatus is the control of air stream temperature close to the tip of the delivery nozzle by means of circulating thermally controlled water around the air delivery tubing.

BRIEF DESCRIPTION OF THE DRAWINGS

Further objects and advantages of the invention will become apparent from the following detailed description of embodiments*, and from the accompany drawings thereof, wherein.

* See /Proctor et al., "Construction of Practical and Inexpensive Air Stimulator for Caloric Vestibular Testing", The Laryngoscope, 86:126–131, 1976 Proctor et al., "A method for Adjusting the Stimulus Intensity of the Air Caloric Test: Preliminary Report", Trans. Am. Acad. Opth. and Otolar., 82:210–222, 1976, features of which are utilized in these embodiments.

DESCRIPTION OF PREFERRED EMBODIMENTS

Aural irrigation with cold or warm fluid causes a temperature difference to appear across the lateral semicircular canal. This temperature difference causes a density difference which moves the endolymph-cupula system. The magnitude of endolymph-displacing forces is nearly proportional to the temperature difference across the semicircular canal, so long as the orientation of the canal with respect to gravity is controlled. Therefore, a knowledge of the temperature difference across the lateral semicircular canal permits a direct estimation of the magnitude of the caloric test stimulus.

The temperature difference across the lateral semicircular canal may be calculated from a knowledge of the irrigation fluid temperature. Furthermore, if the temperature of the irrigating fluid is switched abruptly between hot and cold values, then the timing of this temperature switching can be used to adjust and control the magnitude of the caloric stimulus.

As above stated, to prevent false negative effects, the operator should carefully direct the jet of air against the posterosuperior canal, and it is therefore advantageous to have means to visually monitor the directing of the air stimulation jet.

Figure 1:
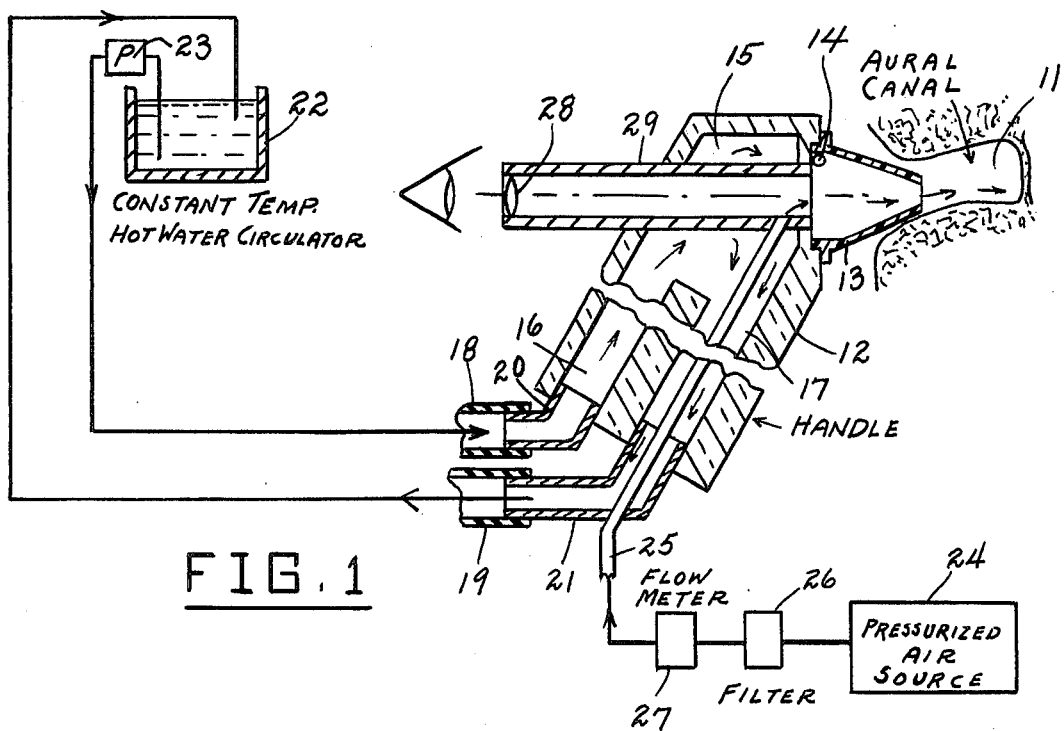
FIG. 1 is a diagrammatic cross-sectional view of an improved visually monitored caloric ear irrigation apparatus in a typical caloric ear irrigation system according to the present invention.

FIG. 1 diagrammatically illustrates a simple caloric air application system including an air-water heat exchanger, according to the present invention, for carrying out a test procedure including the irrigation of an aural canal 11 with heated air as above described, wherein the heat exchanger is incorporated in a handle 12 which is provided at its top forward portion with a conventional frusto-conical ear speculum 13 formed of plastic or the like having a lamp bulb 14 mounted therein in a position to illuminate the interior of the canal 11 when the speculum is inserted in the ear, as shown. A tube 29, of brass for example, is mounted in the top of the handle in alignment with the speculum 13. The handle 12 is formed of suitable insulating material, such as molded Plexiglas, and has an internal chamber 15 through which brass tube 29 extends. The handle 12 has a water inlet passage 16 leading to chamber 15 and an outlet passage 17 leading from said chamber and being in spaced parallel relation with inlet passage 16. Respective flexible inlet and return conduits 18 and 19 are connected to the passages 16 and 17 by means of rigid conduit fittings 20 and 21. Water from a suitably heated constant-temperature bath 22 is circulated by a pump 23 through inlet conduit 18, chamber 15 and return conduit 19.

Air from a pressurized source 24 passes through a conduit 25 including a filter 26 and a flow meter 27. Conduit 25 extends sealingly through and is secured in the wall of return conduit fitting 21 and extends axially through passage 17. The top end of conduit 25 is sealingly secured in and discharges into the brass tube 29 close to its forward end, and forces heated air through said forward end to the speculum 13 to form a jet which can be directed toward the correct location in the aural canal, as viewed through a lens 28 in the rear end of tube 29. Speculum 13 acts as a nozzle.

Thus, the handle 12 serves as a water jacket for the air supply conduit 25, as well as a positioning and visual monitoring means for the irrigating air jet, providing improved visibility of the aural canal 11 during application of the stimulus. Filtered dry air is fed through conduit 25, which in turn is contained within the water jacket defined by passage 17 and chamber 15, which carries the circulating heated water from the water bath 22. The air stream is directed into the viewing tube 29 which is sealed at its viewing end by the lens 28 and communicates at its forward end with speculum 13. The brass tube 29 is bathed by circulating water from the constant-temperature water bath 22. The small electric lamp 14 included in speculum 13 illuminates the aural canal so that the view provided is similar to that of a conventional otoscope.

Figure 2:
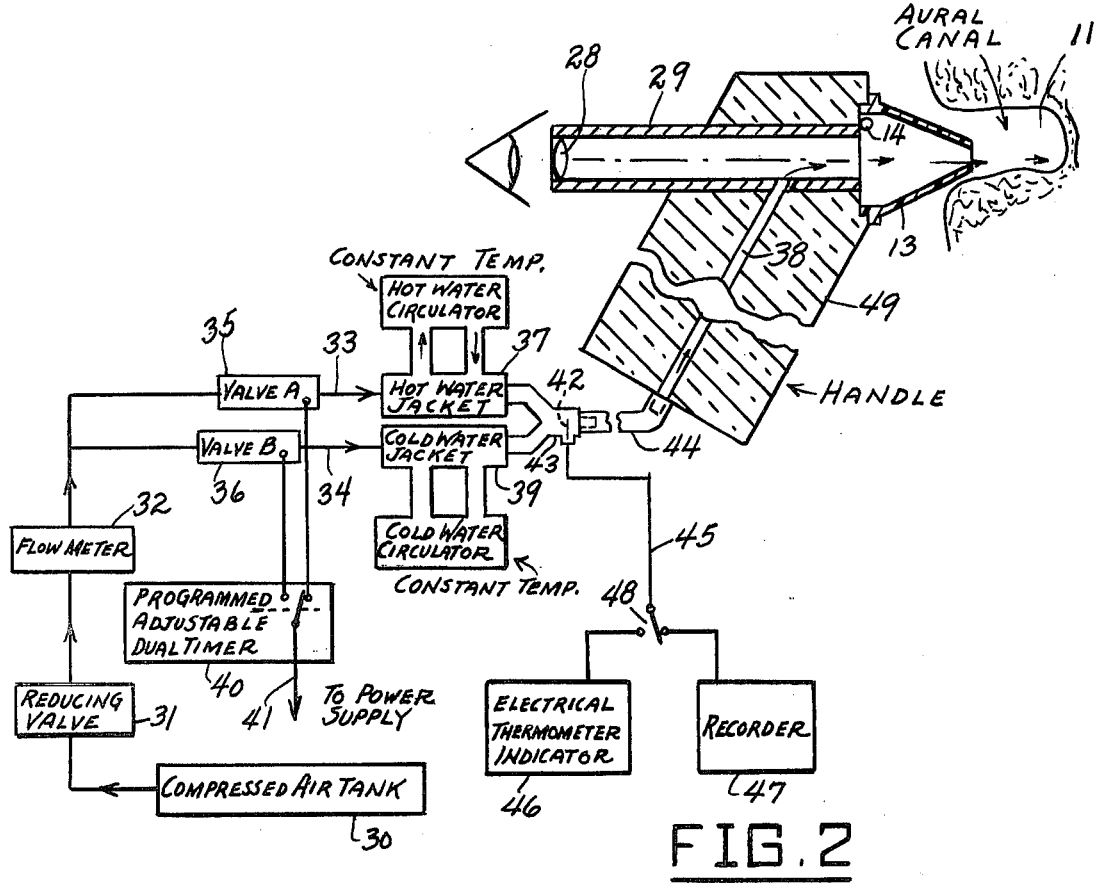
FIG. 2 is a diagrammatic cross-sectional view of another form of improved visually monitored caloric air irrigation apparatus according to the present invention, employing hot and cold air, with means for switching air irrigation temperature between hot and cold values at pre-selected times.

FIG. 2 diagrammatically illustrates a more comprehensive caloric air application system according to the present invention, wherein two heat exchangers are combined with means for rapid switching of the air stream temperature between hot and cold values. Dry air from a compressed air tank 30 is passed through a reducing valve 31 and a flow meter 32 so that it is at controlled pressure, and is supplied thereafter to either a conduit 33 or 34 through an electrically operated control valve 35 or 36. Conduit 33 extends through a hot water jacket 37 and is connected to the applicator air supply conduit 38 via one arm of a Y-fitting 43 and a flexible conduit 44. Conduit 34 extends through a cold water jacket 39 and is connected to said applicator supply conduit 38 via the other arm of the Y-fitting and said flexible conduit 44. The electrical valves 35 and 36 are alternately energized (opened) by an electrical timer 40 connected between the valves and a current supply line 41. The timer 40 has conventional adjustable means for setting the respective alternate periods of energization of the control valves 35 and 36. Thus, the valves 35 and 36 are controlled by the adjustable dual timer 40 so that air flow can be started and directed through either the hot or cold water jacket 37 or 39 at appropriate times. A conventional electrical temperature sensor 42 within the stem of the Y-fitting 43 provides constant monitoring of the air stream temperature at a point just before it enters the flexible conduit 44, which is relatively short, is of low thermal capacity, and is sufficiently insulated to minimize heat loss. The temperature sensor may be mounted closer to the discharge end of the air system if so desired, for example, in the conduit 38 or in the forward end of the brass tube 29 near the speculum 13. The temperature signal line 45 is selectively connected to either a conventional electrical thermometer indicator 46 or a recorder 47 via a 2-position control switch 48.

The conduit 38 is longitudinally mounted in a handle 49 of suitable insulating material, such as Plexiglas, or the like, and extends through the wall of a brass tube 29 mounted in the top portion of the handle. A conventional speculum 13 is suitably secured to the top forward portion of handle 49 in alignment with tube 29, and is provided with a lamp bulb 14, as in the embodiment of FIG. 1. A viewing lens 28 is sealingly secured in the rear end of tube 29.

In a typical cycle of operation, using the system of FIG. 2, aural irrigation may be begun with warm air, for example, at 51° C, switched to cool air, for example, at 23° C, and then switched back to the warm air at 51° C. Under these conditions, the duration of the initial 51° C irrigation determines the magnitude of the caloric stimulus produced during the initial hot phase of the stimulation. In a similar way, the duration of the second irrigation, at 23° C, determines the magnitude of the resulting caloric stimulus during the cold phase of the reaction.

The system of FIG. 2 may be employed with suitable hot and cold phase durations to produce a desired graded series of stimulus magnitudes. Thus, the caloric stimulus can be controlled and adjusted in a consistent manner by employing the appropriate set of irrigation durations. With said selected set of irrigation durations applied to a patient, a biphasic nystagmus pattern may be recorded, using conventional eye movement sensing and recording apparatus providing an electronystagmographic curve or trace.

Furthermore, a patient may be tested for vestibular responses by comparing his responses to weak stimulations with those produced by stronger stimulations. In order to perform this type of test, a monophasic stimulus pattern may be employed, for example, wherein only the first (hot) phase of the stimulus appears. For monophasic testing the irrigation temperature is switched only once, thereby simply terminating the initial (hot) irrigation with a brief cold irrigation sufficient to reduce the temperature change caused by the previous hot irrigation to zero, namely, to remove the temperature increment across the lateral semicircular canal. Using a series of independent monophasic stimulations of increasing magnitudes provides a way of measuring nystagmus response intensity as a function of stimulus intensity, and can be employed to compare responses of the right ear with those of the left ear, to thereby detect and diagnose abnormalities causing reduced response, such as vestibular neuronitis.

It will be seen that among the advantages of a caloric irrigation technique as above described, using the disclosed apparatus, are reduced required duration of action of the caloric stimulus and the ability of easily adjust the intensities of the individual stimulations; the provision for visual monitoring of the area being irrigated enables testing to be performed without "false negative" reactions. Prompt removal of the caloric stimulus permits a reduction in the waiting time between irrigations, as well as reduces interaction among successive stimulations. Stimulus intensity can be easily reduced for those subjects who are unusually sensitive, or increased when responses are feeble. In addition, a series of stimulations of various intensities may be applied to explore other aspects of vestibular responsiveness.

In both of the embodiments of FIGS. 1 and 2, the parts carried by the handle 12 or 49 are preferably detachably secured to the handle so that the irrigation applicator can be disassembled for cleaning or repairs.

While certain specific embodiments of improved caloric testing apparatus for introducing heated or cooled air, under direct visual control, have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. An apparatus for stimulating an aural canal of a patient comprising an insulating handle member, means to view the aural canal of an ear comprising a viewing tube having a forward discharge end and a rear end and mounted on said handle member and having frusto-conical nozzle means at its forward end adapted to be inserted in a patient's ear to continuously pass alternately heated and cooled gas to the aural canal and then out of the aural canal, a source of pressurized gas, conduit means connecting said source to said viewing tube and passing through said insulating handle, and means for precisely controlling the temperature of gas entering the aural canal comprising heat exchanger means surrounding at least a portion of said conduit means, the location of said heat exchanger means relative to said nozzle means being such that the temperature of said gas entering the aural canal is precisely controlled.

2. The apparatus of claim 1, and a lens sealingly mounted in the rear end of said viewing tube.

3. The apparatus of claim 2, and lamp means in said frusto-conical nozzle means arranged to illuminate the interior of the patient's ear.

4. The apparatus of claim 1, and wherein said conduit means extends longitudinally through said handle member.

5. The apparatus of claim 1, and wherein said insulating handle member is formed with a cavity around a portion of said conduit means and wherein said heat exchanger means comprises a source of temperature controlled fluid connected to said cavity.

6. The apparatus of claim 1, and wherein said heat exchanger means comprises a heated liquid container, liquid jacket means surrounding said conduit means located in said handle, and means to circulate heated liquid from said container through said jacket means.

7. The apparatus of claim 1, and wherein said conduit means comprises an applicator supply conduit connected to said viewing tube, two respective branch conduits connected to said applicator supply conduit, and means to selectively connect said source of pressurized gas to said branch conduits, and wherein said heat exchanger means comprises respective jacket means surrounding said branch conduits, respective sources of heated and cold liquid, and means to circulate liquid from the heated and cold liquid sources respectively through said jacket means.

8. The apparatus of claim 7, and wherein said selective connecting means comprises respective valves in the branch conduits.

9. The apparatus of claim 8, and means to alternately operate said valves for selected time periods.

10. The apparatus of claim 8, and temperature-sensing means in the path of gas flow between said branch conduits and said frusto-conical nozzle means.

* * * * *